(12) United States Patent
Hanano

(10) Patent No.: US 12,171,400 B2
(45) Date of Patent: Dec. 24, 2024

(54) ILLUMINATION OPTICAL SYSTEM AND ILLUMINATION DEVICE

(71) Applicant: OLYMPUS CORPORATION, Tokyo (JP)

(72) Inventor: Kazunari Hanano, cHachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 17/546,479

(22) Filed: Dec. 9, 2021

(65) Prior Publication Data

US 2022/0095896 A1  Mar. 31, 2022

Related U.S. Application Data

(63) Continuation of application No. PCT/JP2019/024794, filed on Jun. 21, 2019.

(51) Int. Cl.

| | |
|---|---|
| *A61B 1/00* | (2006.01) |
| *A61B 1/06* | (2006.01) |
| *A61B 1/07* | (2006.01) |
| *F21V 8/00* | (2006.01) |
| *G02B 19/00* | (2006.01) |
| *G02B 23/24* | (2006.01) |

(52) U.S. Cl.
CPC ............ *A61B 1/00096* (2013.01); *A61B 1/07* (2013.01); *G02B 6/0006* (2013.01); *G02B 23/2469* (2013.01); *A61B 1/0661* (2013.01); *G02B 19/0057* (2013.01)

(58) Field of Classification Search
CPC ..... A61B 1/00096; A61B 1/07; A61B 1/0661; G02B 6/0006; G02B 23/2469; G02B 19/0057; G02B 6/0008; G02B 6/3624; G02B 6/4298; G02B 19/0052
See application file for complete search history.

(56) References Cited

U.S. PATENT DOCUMENTS

| | | | |
|---|---|---|---|
| 9,880,380 B2 * | 1/2018 | Daidoji | ................ G02B 6/3598 |
| 10,912,452 B2 * | 2/2021 | Yamana | ............ G02B 23/2469 |
| 2004/0062044 A1 * | 4/2004 | Hanano | .............. G02B 27/0955 362/317 |

(Continued)

FOREIGN PATENT DOCUMENTS

| | | |
|---|---|---|
| JP | 2004-248834 A | 9/2004 |
| JP | 2011-224044 A | 11/2011 |

(Continued)

OTHER PUBLICATIONS

International Search Report dated Aug. 27, 2019 received in PCT/JP2019/024794.

*Primary Examiner* — Collin X Beatty

(74) *Attorney, Agent, or Firm* — Scully, Scott, Murphy & Presser, P.C.

(57) ABSTRACT

An illumination optical system includes: a condenser lens; a first light guiding member configured to guide the light input to a first entrance end face by reflecting the light inside the condenser lens, and output the light from a first exit end face; a pupil generating lens configured to generate a pupil with the first exit end face serving as an object surface; and a second light guiding member configured to guide the light input to a second entrance end face by reflecting the light inside the second light guiding member, and output the light from a second exit end face.

11 Claims, 18 Drawing Sheets

(56) References Cited

U.S. PATENT DOCUMENTS

2014/0005483 A1\* 1/2014 Ohashi ................ A61B 1/0646
600/162
2017/0115478 A1 4/2017 Fujii et al.

FOREIGN PATENT DOCUMENTS

| JP | 2013-090706 A | 5/2013 |
| JP | 2014-008316 A | 1/2014 |
| JP | 2014-121363 A | 7/2014 |
| JP | 2016-179009 A | 10/2016 |

\* cited by examiner

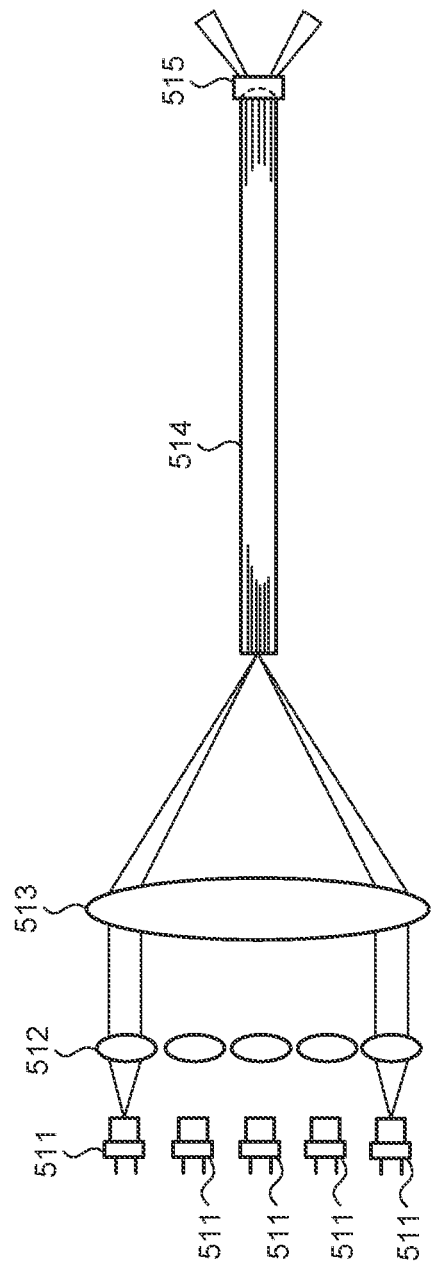

ILLUMINATION OPTICAL SYSTEM AND ILLUMINATION DEVICE

This application is a continuation of International Application No. PCT/JP2019/024794, filed on Jun. 21, 2019, the entire contents of which are incorporated herein by reference.

BACKGROUND

The present disclosure relates to illumination optical systems and illumination devices.

Endoscope systems for in-vivo observation of subjects have been used in the medical field. Typically, in observation using an endoscope, an elongated flexible insertion unit is inserted into a subject, such as a patient, and the interior of the subject is illuminated with illumination light from a distal end of this insertion unit. This illumination light is supplied to the insertion unit by a light source device. An imaging unit at the distal end of the insertion unit of the endoscope captures in-vivo images by receiving reflected light of the illumination light. These in-vivo images captured by the imaging unit are displayed on a display of an endoscope system after being subjected to predetermined image processing at a processing device connected to the endoscope. A user, such as a medical doctor, conducts observation of organs of the subject, on the basis of these in-vivo images displayed on the display.

A known device for emitting such illumination light involves a technique of forming light emitted by each of plural light sources into collimated light by means of collimator lenses and thereafter condensing the collimated light by means of a condenser lens and causing the condensed collimated light to enter a light guide (see, for example, Japanese Patent Application Laid-open No. 2013-90706). According to this patent application, the collimated light is guided by the light guide and a subject is irradiated with the collimated light that has been guided. Furthermore, according to this patent application, some of the plural light sources are arranged at positions where light is perpendicularly input to an entrance face of the light guide via the collimator lenses and condenser lens and the other light sources are arranged at positions where light is diagonally input to the entrance face of the light guide.

SUMMARY

According to one aspect of the present disclosure, there is provided an illumination optical system including: a condenser lens configured to condense plural light fluxes incident on different positions on a surface of the condenser lens; a first light guiding member including a first entrance end face to which light condensed by the condenser lens is input, and a first exit end face from which the light is output, the first light guiding member being configured to guide the light input to the first entrance end face by reflecting the light inside the condenser lens, and output the light from the first exit end face; a pupil generating lens to which the light output from the first exit end face is input, the pupil generating lens being configured to generate a pupil with the first exit end face serving as an object surface; and a second light guiding member including a second entrance end face arranged at a position of the pupil or a position conjugate to the position of the pupil, the light passed through the pupil generating lens being input to the second entrance end face, and a second exit end face from which the light that input to the second entrance end face is output, the second light guiding member being configured to guide the light input to the second entrance end face by reflecting the light inside the second light guiding member, and output the light from the second exit end face.

According to another aspect of the present disclosure, there is provided an illumination optical system including: a condenser lens configured to condense plural light fluxes incident on different positions on a surface of the condenser lens; a first light guiding member including a first entrance end face to which light condensed by the condenser lens is input, and a first exit end face from which the light is output, the first light guiding member being configured to guide the light input to the first entrance end face by reflecting the light inside the condenser lens, and output the light from the first exit end face; a pupil generating lens to which the light output from the first exit end face is input, the pupil generating lens having a focal position, toward the first light guiding member, being arranged at the first exit end face; and a second light guiding member including a second entrance end face arranged at a position of a pupil of the pupil generating lens or a position conjugate to the position of the pupil, the light passed through the pupil generating lens being input to the second entrance end face, and a second exit end face from which the light is output, the second light guiding member being configured to guide the light input to the second entrance end face by reflecting the light inside the second light guiding member, and output the light from the second exit end face.

According to still another aspect of the present disclosure, there is provided an illumination optical system including: a condenser lens configured to condense plural light fluxes incident on different positions on a surface of the condenser lens; a first light guiding member including a first entrance end face to which light condensed by the condenser lens is input, and a first exit end face from which the light is output, the first light guiding member being configured to guide the light input to the first entrance end face by reflecting the light inside the condenser lens, and output the light from the first exit end face; a second light guiding member including a second entrance end face to which the light output from the first exit end face is input, and a second exit end face from which the light is output, the second light guiding member being configured to guide the light input to the second entrance end face by reflecting the light inside the second light guiding member, and output the light from the second exit end face; and a Kohler illumination unit configured to provide Kohler illumination to the second entrance end face with the light output from the exit end face, wherein a pupil plane of the whole optical system from the condenser lens to the Kohler illumination unit is arranged at the second entrance end face.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 22B is a diagram illustrating light sources turned on according to the known illumination technique and a light distribution thereof.

DETAILED DESCRIPTION

Modes for implementing the present disclosure (hereinafter, referred to as "embodiments") will be described below. With respect to the embodiments, a medical endoscope system for capturing and displaying in-vivo images of subjects, such as patients, will be described as an example of a system including an illumination optical system and an illumination device according to the present disclosure. The present disclosure is not limited by these embodiments. The drawings will be described by assigning the same reference sign to portions that are the same.

First Embodiment

Figure 1:
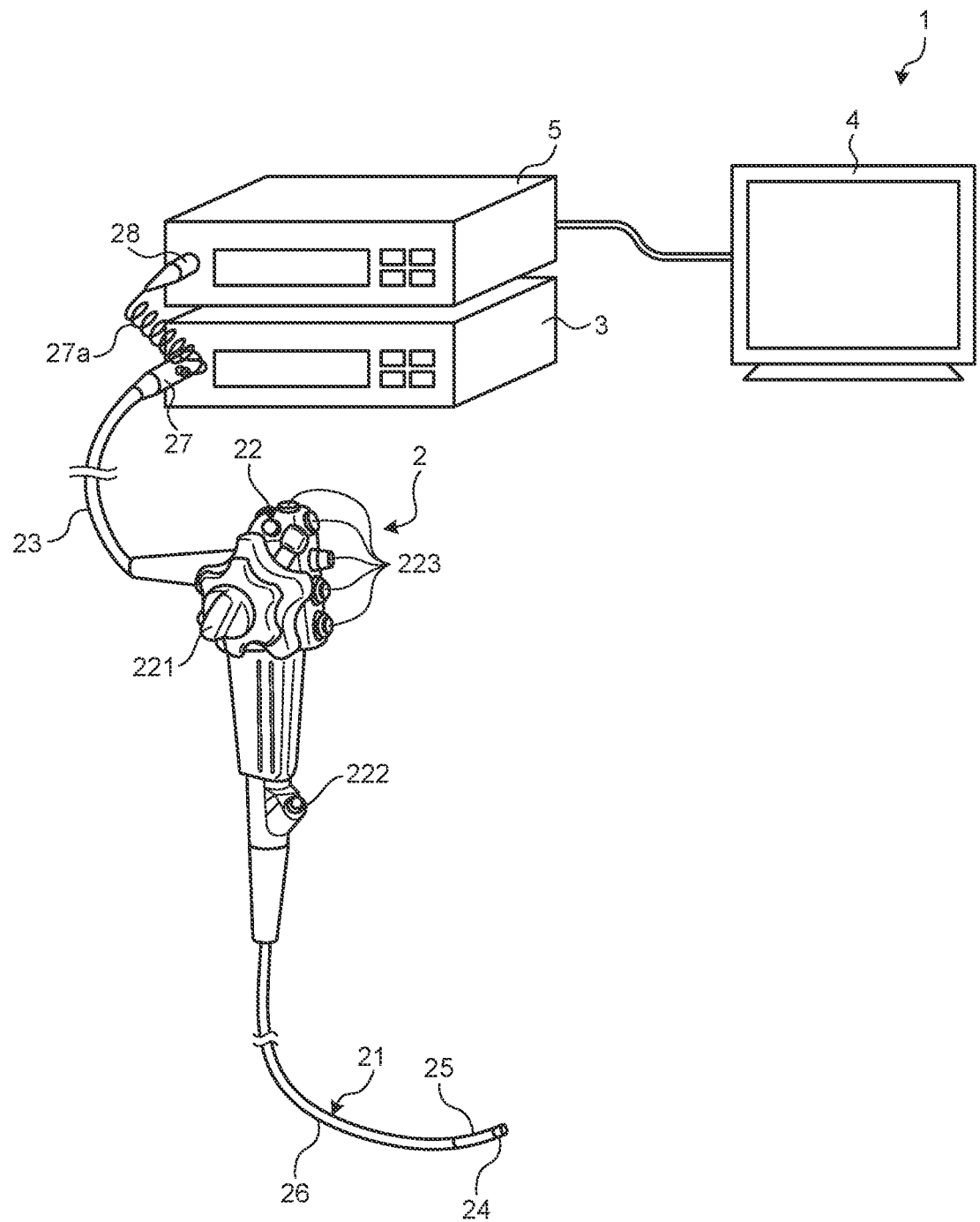
FIG. 1 is a diagram illustrating a schematic configuration of an endoscope system according to a first embodiment.
Figure 2:
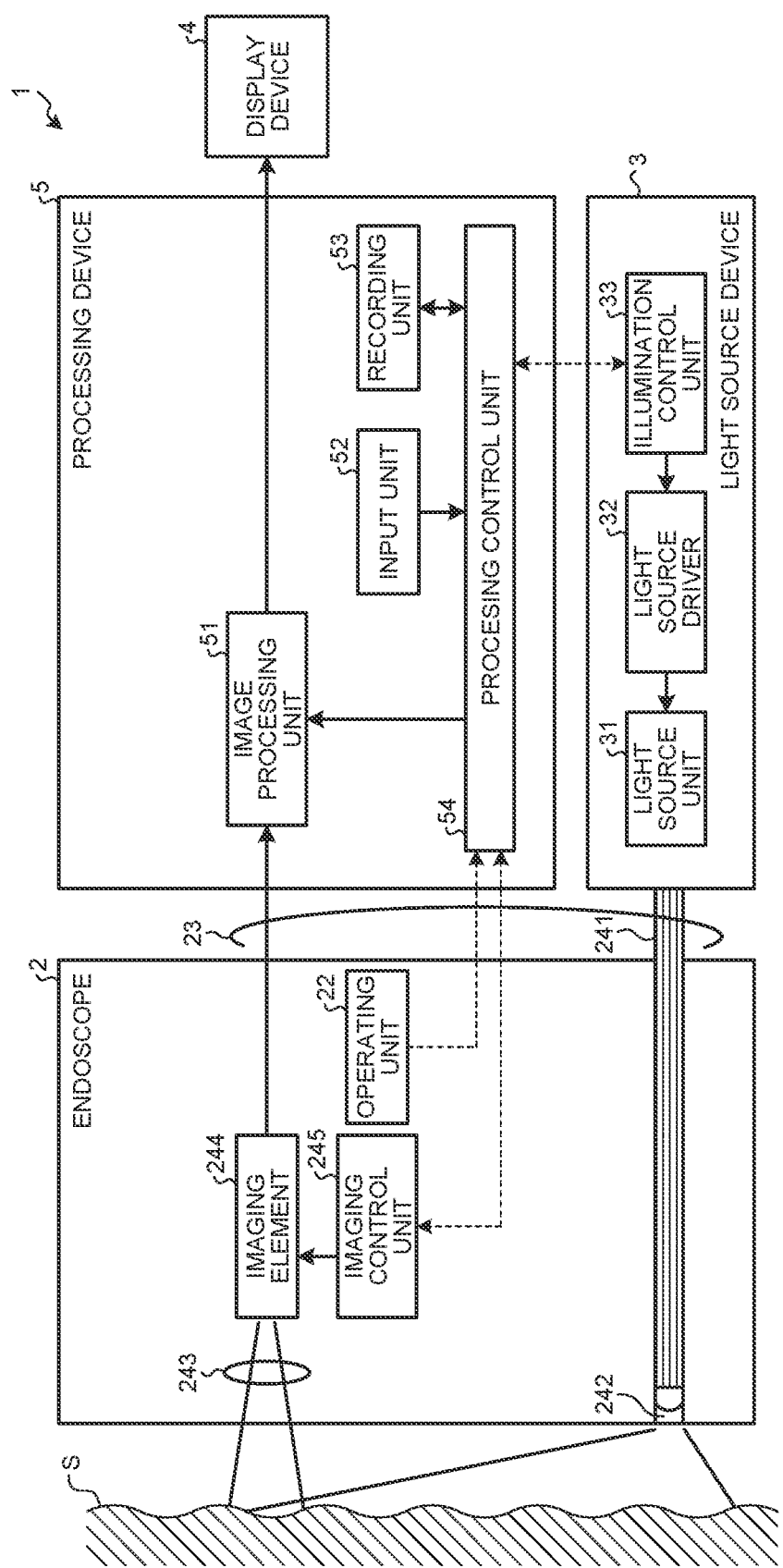
FIG. 2 is a block diagram illustrating a schematic configuration of the endoscope system according to the first embodiment.

FIG. 1 is a diagram illustrating a schematic configuration of an endoscope system according to a first embodiment. FIG. 2 is a block diagram illustrating a schematic configuration of the endoscope system according to the first embodiment.

An endoscope system 1 illustrated in FIG. 1 and FIG. 2 captures images of the interior (a subject S) of a subject, such as a patient, by insertion of an endoscope into the subject, and outputs data on the images captured, to an external display device. By conducting observation of in-vivo images displayed at the display device, a user, such as a medical doctor, checks for any bleeding site, tumor site, and abnormal site that are sites to be detected. The endoscope system 1 includes an endoscope 2, a light source device 3, a display device 4, and a processing device 5 (a processor).

The endoscope 2 captures images of the interior of a subject to generate image data and outputs the image data generated, to the processing device 5. The endoscope 2 includes an insertion unit 21, an operating unit 22, and a universal cord 23.

The insertion unit 21 has an elongated shape having flexibility. The insertion unit 21 has: a distal end portion 24 having an imaging element 244 described later and built therein; a bending portion 25 that is formed of plural bending pieces and is freely bendable; and a flexible tube portion 26 that is connected to a proximal end of the bending portion 25, has flexibility, and is elongated.

The distal end portion 24 has a light guide 241 that forms a light guiding path for light emitted by the light source device 3, an illumination lens 242 provided at a distal end of the light guide 241, an optical system 243 for condensing light, the imaging element 244 provided at an image forming position of the optical system 243 and having plural pixels that receive light beams condensed by the optical system 243, photoelectrically convert the light beams into electric signals, and are arranged two-dimensionally, and an imaging control unit 245 that controls the imaging element 244. The light guide 241 corresponds to a second light guiding member.

The imaging element 244 is formed using an image sensor, such as a charge coupled device (CCD) or a complementary metal oxide semiconductor (CMOS). Specifically, the imaging element 244 has plural pixels that output electric signals by receiving light beams and photoelectrically converting the light beams, the plural pixels being arranged two-dimensionally, and the imaging element 244 captures images of the subject S (for example, a body cavity) at a predetermined frame rate to output image data (for example, RAW data).

The endoscope 2 has a memory (not illustrated in the drawings) that stores: an execution program and a control program, for the imaging element 244 to execute various operations; and data including identification information on the endoscope 2. The identification information includes, for example, unique information (ID), the model year, specification information, and the transmission scheme, of the endoscope 2. Furthermore, the memory may temporarily store image data generated by the imaging element 244, for example.

The operating unit 22 has: a bending knob 221 configured to bend the bending portion 25 upward, downward, leftward, and rightward; a treatment tool insertion unit 222 from which treatment tools, such as biological forceps, a laser scalpel, and an examination probe, are inserted into a body cavity; and plural switches that are an operation input unit that inputs: operation instruction signals for, in addition to the light source device 3 and processing device 5, peripheral devices, such as an air feeding means, a water feeding means, and a gas feeding means; and an imaging instruction signal for instructing the imaging element 244 to capture still images. A treatment tool inserted from the treatment tool insertion unit 222 comes out from an opening (not illustrated in the drawings) via a treatment tool channel (not illustrated in the drawings) in the distal end portion 24.

The universal cord 23 has, built therein, at least the light guide 241 and an assembly cable having one or plural cables bundled together. The assembly cable is a signal line for transmitting and receiving signals to and from the endoscope 2 and light source device 3 from and to the processing device 5, and includes a signal line for transmitting and receiving setting data, a signal line for transmitting and receiving image data, and a signal line for transmitting and receiving a timing signal for driving the imaging element 244. The universal cord 23 has a connector 27 that is attachable to and detachable from the light source device 3. The connector 27 has a coil cable 27a that is coiled and provided to extend from the connector 27. A connector 28 that is attachable to and detachable from the processing device 5 is provided at an extended end of the coil cable 27a.

The light source device 3 supplies illumination light to be emitted to a subject, from the distal end portion 24 of the endoscope 2. The light source device 3 includes a light source unit 31, a light source driver 32, and an illumination control unit 33.

The light source unit 31 emits illumination light with which a subject is to be irradiated, on the basis of electric current supplied from the light source driver 32. A configuration of the light source unit 31 will be described later.

Under control of the illumination control unit 33, the light source driver 32 causes the light source unit 31 to emit illumination light by supplying electric current to the light source unit 31.

The illumination control unit 33 controls, on the basis of an instruction signal received from the processing device 5, lighting of light sources included in the light source unit 31. The illumination control unit 33 controls light sources to be turned on, according to a light intensity value acquired on the basis of the instruction signal. The illumination control unit 33 is formed using a general-purpose processor, such as a central processing unit (CPU), or a special-purpose processor, such as various arithmetic circuits that execute specific functions, like an application specific integrated circuit (ASIC).

The display device 4 displays an image corresponding to image data generated by the endoscope 2 and received from the processing device 5. The display device 4 displays various types of information related to the endoscope system 1. The display device 4 is formed using a display panel of liquid crystal or organic electroluminescence, for example.

The processing device 5 receives image data generated by the endoscope 2, performs predetermined image processing on the image data received, and outputs the image data processed, to the display device 4. Furthermore, the processing device 5 integrally controls the overall operation of the endoscope system 1. The processing device 5 includes an image processing unit 51, an input unit 52, a recording unit 53, and a processing control unit 54.

Under control of the processing control unit 54, the image processing unit 51 receives image data generated by the endoscope 2, performs predetermined image processing on the image data received, and outputs the image data processed, to the display device 4. The predetermined image processing may include, for example, interpolation processing, OB clamp processing, gain adjustment processing, and format conversion processing. The image processing unit 51 is formed using a graphics processing unit (GPU), digital signal processing (DSP), or a field programmable gate array (FPGA), for example.

The input unit 52 receives input of an instruction signal for instructing an operation of the endoscope system 1 and outputs the instruction signal received, to the processing control unit 54. The input unit 52 is formed using switches, buttons, and a touch panel, for example.

The recording unit 53 records therein various programs executed by the endoscope system 1, data being executed by the endoscope system 1, and image data generated by the endoscope 2. The recording unit 53 is formed using a volatile memory, a non-volatile memory, and a memory card, for example.

The processing control unit 54 is formed using a CPU or an ASIC, for example. The processing control unit 54 controls each unit forming the endoscope system 1.

Figure 3:
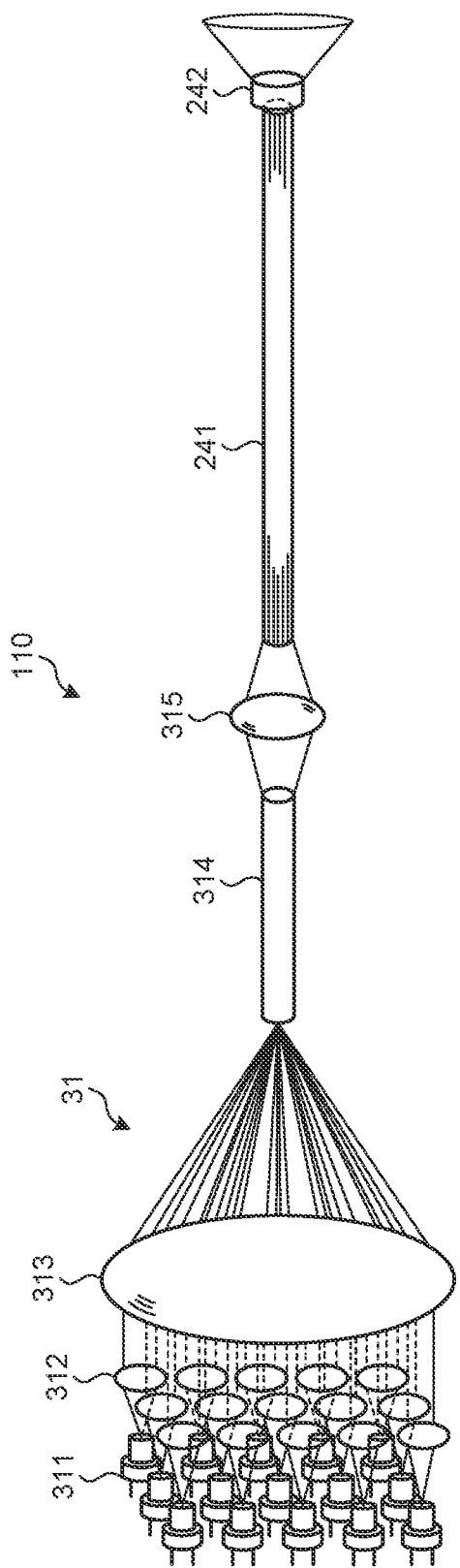
FIG. 3 is a perspective view illustrating a configuration of an illumination device included in the endoscope system according to the first embodiment.
Figure 4:
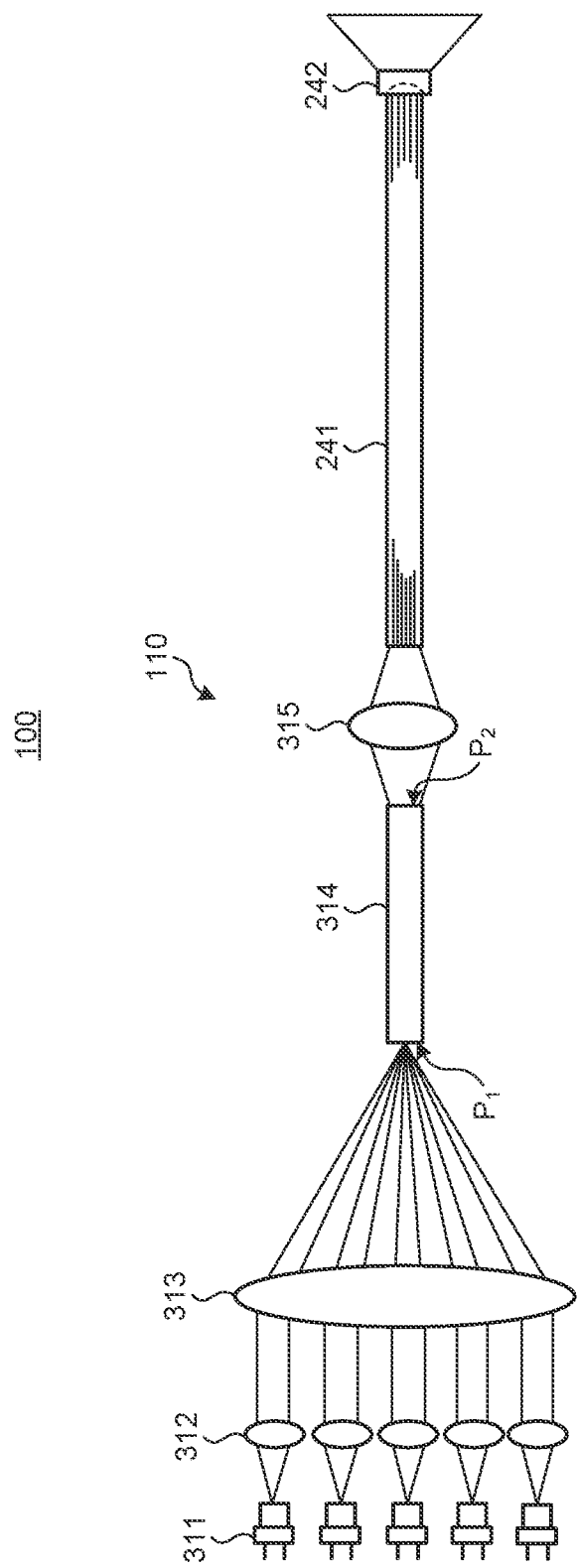
FIG. 4 is a diagram illustrating a configuration of the illumination device included in the endoscope system according to the first embodiment.

An illumination device configured to include the light source unit 31, the light guide 241, and the illumination lens 242 will be described next by reference to FIG. 3 and FIG. 4. FIG. 3 is a perspective view illustrating a configuration of the illumination device included in the endoscope system according to the first embodiment. FIG. 4 is a diagram illustrating a configuration of the illumination device included in the endoscope system according to the first embodiment. FIG. 4 is a plan view illustrating only light sources and collimator lenses that are positioned on a plane passing an optical axis of an illumination device 100, of plural light sources and collimator lenses that are illustrated in FIG. 3.

Specifically, the illumination device 100 includes plural light sources 311, plural collimator lenses 312, a condenser lens 313, a rod 314, a pupil generating lens 315, the light guide 241, and the illumination lens 242. Of these, the plural light sources 311, the plural collimator lenses 312, the condenser lens 313, and the rod 314 form the light source unit 31. Furthermore, in this first embodiment, the collimator lenses 312, the condenser lens 313, the rod 314, the pupil generating lens 315, the light guide 241, and the illumination lens 242 form an illumination optical system 110. The condenser lens 313 corresponds to a first lens. The rod 314 corresponds to a first light guiding member. The pupil generating lens 315 corresponds to a second lens.

The light sources 311 emit illumination light. The light sources 311 are formed using coherent and highly directional light sources, for example, semiconductor lasers (semiconductor light sources). The light sources 311 emit illumination light formed of white light or light of a specific wavelength band.

The collimator lenses 312 are provided correspondingly to the respective light sources 311 and form illumination light emitted by the light sources 311 into approximately collimated light. The collimator lenses 312 form illumination light emitted by the light sources 311 into light parallel to the optical axis of the illumination device 100, or into light that travels in a direction inclined, in a range allowing the light to be condensed by the condenser lens 313, with respect to this optical axis.

The condenser lens 313 condenses light (collimated light) that has passed through the collimator lenses 312 and enters the condenser lens 313. The condenser lens 313 condenses plural light fluxes that have passed through the respective collimator lenses 312 and differ in height from a central axis of the lens. This "height from a central axis of the lens" herein means a position along a direction (radial direction) orthogonal to the central axis in a case where the lens has a circular outer circumference, for example. In other words, the condenser lens 313 condenses plural approximately collimated light beams (light fluxes) respectively incident on different positions on a surface of the lens.

The rod 314 is provided at the condensing position of the condenser lens 313, and light condensed by the condenser lens 313 is input to the rod 314. The rod 314 has an entrance end face $P_1$ (a first entrance end face) to which light from the condenser lens 313 is input and an exit end face $P_2$ (a first exit end face) which is provided opposite to the entrance end face and from which the light that has entered the rod 314 is output, and the rod 314 guides the light from the entrance end face to the exit end face while reflecting the light. The rod 314 reflects light at a boundary surface between the rod 314 and the outside. The rod 314 guides the light from the entrance end face to the exit end face through repetition of the reflection of the light inside the rod 314. The rod 314 is formed using a rod integrator that uniformizes the spatial intensity distribution of light in the plane of the exit end face.

In FIG. 3, the plural light sources 311 are arranged in a two-dimensional array. Rays of light respectively emitted from the plural light sources 311 enter the condenser lens 313 after being collimated by the respective collimator lenses 312, and are condensed onto the entrance end face of the rod 314. A configuration of the light source unit 31 is not limited to the configuration already described, and various modifications thereof are possible. For example, the plural light sources 311 may each be arranged near the spherical center of a concave mirror to emit light toward a concave surface, such that rays of light reflected by the concave mirror enter the condenser lens 313 and are condensed onto the entrance end face of the rod 314.

Light output from the exit end face of the rod 314 enters the pupil generating lens 315 that generates a pupil, with this exit end face serving as an object surface. Furthermore, the exit end face $P_2$ of the rod 314 is arranged at a focal position of the pupil generating lens 315, the focal position being toward the rod 314. The pupil generating lens 315 corresponds to a Kohler illumination unit that provides Kohler illumination to an entrance end face (an entrance end face $P_3$ described later) of the light guide 241, with light output from the exit end face $P_2$.

The light guide 241 has an entrance end face (a second entrance end face) to which light from the pupil generating lens 315 is input and an exit end face (a second exit end face) which is provided opposite to the entrance end face and from which light that has entered the light guide 241 is output, and the light guide 241 guides the light from the entrance end face to the exit end face. The entrance end face of the light guide 241 is arranged at the position of the pupil generated by the pupil generating lens 315, that is, in a pupil plane region near and including a pupil plane of the whole optical system from the condenser lens 313 to the pupil generating lens 315 (the Kohler illumination unit). The pupil plane herein refers to the plane on which the pupil is formed. In this first embodiment, the light guide 241 is formed using a fiber bundle which is formed of a bundle of plural optical fibers with facets of the plural optical fibers aligned with one another, and light emitted from the exit end face of the light guide 241 has an output angle dependent on the incident angle of light incident on the entrance end face of the light guide 241. The light guide 241 corresponds to a second light guiding member.

The illumination lens 242 emits light that has been input via the light guide 241, to the outside at a wider angle, for example.

In the illumination optical system 110, optical axes of the optical system formed of the collimator lenses 312, the condenser lens 313, the rod 314, and the pupil generating lens 315 coincide with one another.

Figure 5:
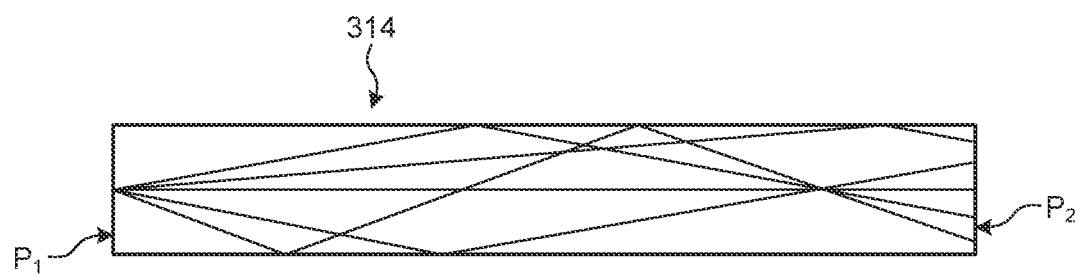
FIG. 5 is a diagram illustrating an example of propagation of light in a rod included in a light source unit.

FIG. 5 is a diagram illustrating an example of propagation of light in a rod included in a light source unit. Light beams that have entered the rod 314 from the entrance end face $P_1$ via the condenser lens 313 are respectively reflected at points to which the light beams travels and reach the exit end face $P_2$.

Figure 6:
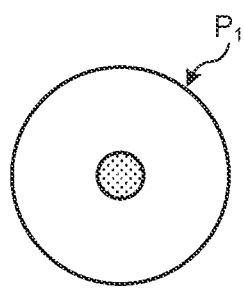
FIG. 6 is a diagram illustrating a distribution of light at an entrance end face $P_1$ illustrated in FIG. 5.
Figure 7:
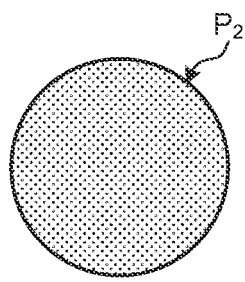
FIG. 7 is a diagram illustrating a distribution of light at an exit end face $P_2$ illustrated in FIG. 5.

FIG. 6 is a diagram illustrating a distribution of light at the entrance end face $P_1$ illustrated in FIG. 5. FIG. 7 is a diagram illustrating a distribution of light at the exit end face $P_2$ illustrated in FIG. 5. Light incident on the entrance end face $P_1$ has been condensed by the condenser lens 313, and thus is distributed in a part of the entrance end face $P_1$ (represented by hatching in a central portion in FIG. 6). In contrast, light that has reached the exit end face $P_2$ via the interior of the rod 314 is distributed over the whole exit end face $P_2$ (see FIG. 7). Spatial intensity distribution of light that has entered the rod 314 becomes uniform at the exit end face by traveling through the rod 314 having a predetermined length in a longitudinal direction thereof.

Incoming angles of light beams incident on the rod 314 from the condenser lens 313 differ depending on the arrangement of the light sources 311 relative to the condenser lens 313. The incoming angle referred to herein is the angle formed between the traveling direction of the light and the optical axis direction of the rod 314 (corresponding herein to the longitudinal direction of the rod 314).

Figure 8:
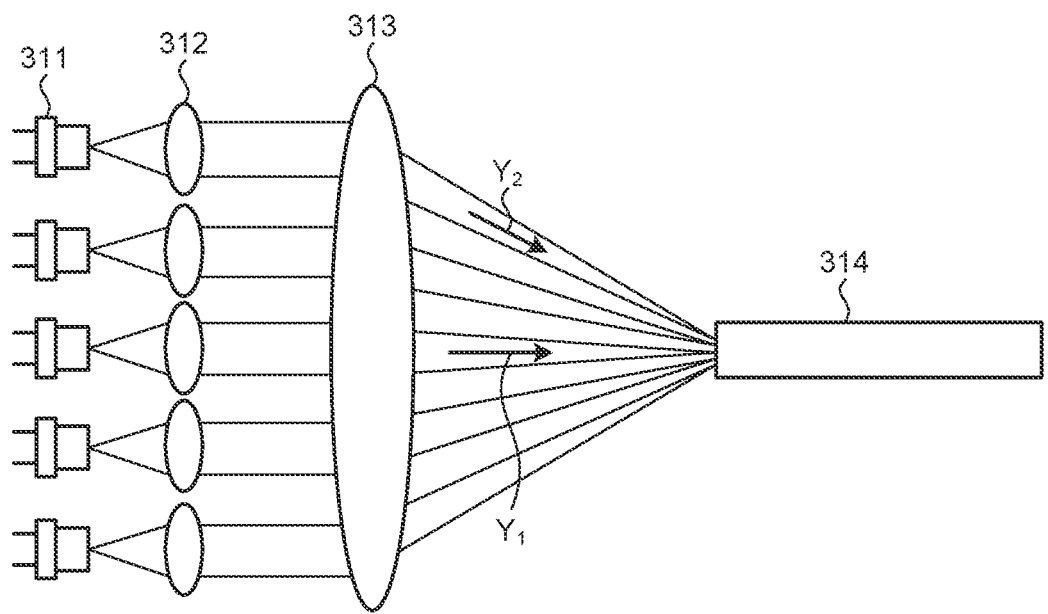
FIG. 8 is a diagram illustrating an example of propagation paths of light beams, from light sources to their incidence on the rod, in the light source unit.

FIG. 8 is a diagram illustrating an example of propagation paths of light beams, from light sources to incidence on a rod, in the light source unit. For example, in FIG. 8, the farther a light source is from the center of the condenser lens 313, the larger the incoming angle to the rod 314 of the light beam emitted by that light source is. Specifically, a light beam (an arrow $Y_2$) emitted by a light source arranged at a position far from the center of the condenser lens 313 has a larger incoming angle than that of a light beam (an arrow $Y_1$) emitted by a light source arranged at a position in a central region near and including the center of the condenser lens 313.

Figure 9:
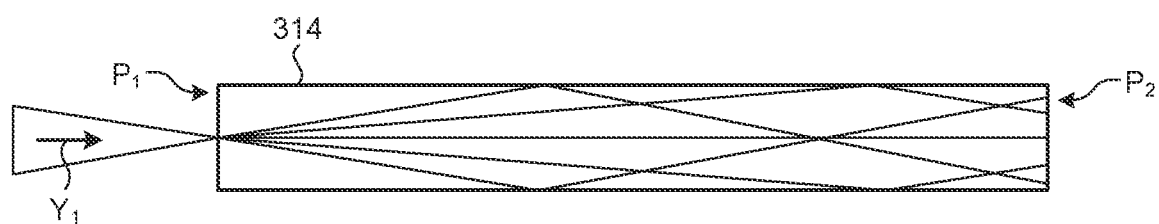
FIG. 9 is a diagram illustrating an example of light guiding paths in the rod for light that travels in a direction of an arrow $Y_1$ illustrated in FIG. 8.
Figure 10:
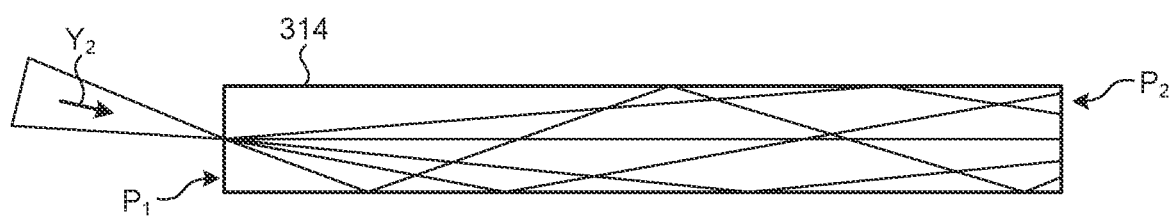
FIG. 10 is a diagram illustrating an example of light guiding paths in the rod for light that travel in a direction of an arrow $Y_2$ illustrated in FIG. 8.

FIG. 9 is a diagram illustrating an example of light guiding paths in the rod for the light that travels in the direction of the arrow $Y_1$ illustrated in FIG. 8. FIG. 10 is a diagram illustrating an example of light guiding paths in the rod for light that travels in the direction of the arrow $Y_2$ illustrated in FIG. 8. The arrows $Y_1$ and $Y_2$ each indicate the traveling direction of the light beam positioned in the center of the light flux. FIG. 9 and FIG. 10 illustrate examples of traveling paths in the rod 314 for (some of) components forming light incident on the rod 314.

Even if these light beams have different incoming angles to the rod 314, by being reflected in the rod 314, the light beams both have uniform spatial intensity distributions at the exit end face $P_2$ (for example, see FIG. 7). That is, by being reflected in the rod 314, light that has entered the rod 314 becomes approximately uniform in spatial intensity distribution regardless of the incoming angle.

Figure 11:
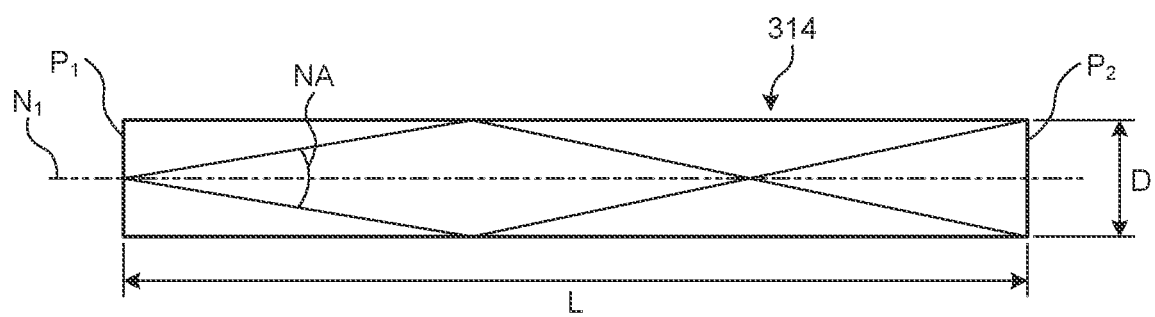
FIG. 11 is a diagram illustrating a relation between uniformity of light and length in the rod included in the light source unit.

Setting of the length of the rod 314 will be described next by reference to FIG. 11. FIG. 11 is a diagram illustrating a relation between uniformity of light and length in the rod included in the light source unit. When the length of the rod 314 in its longitudinal direction (a central axis $N_1$ direction) is L, the diameter of the rod 314 is D, and the numerical aperture is NA, the length L of the rod 314 for causing light to be reflected twice or more inside the rod 314 is calculated by Equation (1) below. The numerical aperture NA is expressed by n×sin θ when the largest angle of light incident on the rod 314 from the outside is θ with respect to the optical axis (central axis $N_1$) of the rod 314, and the refractive index of a medium between the outside space and the rod 314 is n.

$$L > 3D/NA \qquad (1)$$

Equation (1) above enables determination of the length L of the rod 314 that enables the spatial intensity distribution to be uniform. In other words, the rod 314 that enables the spatial intensity distribution to be uniform satisfies Equation (1) above.

Light beams from the light sources 311 are mixed by entering the rod 314 via the collimator lenses 312 and condenser lens 313 and repeating reflection inside the rod 314, and light uniform in spatial intensity distribution is thereby generated. The larger the number of times the light from each light source is reflected, that is, the longer the length of the rod 314, the more solved the unevenness due to the positional differences among the light sources 311, and the more achieved the effect of uniformizing the spatial intensity distribution.

Light that has become uniform in spatial intensity distribution enters the pupil generating lens 315.

Figure 12:
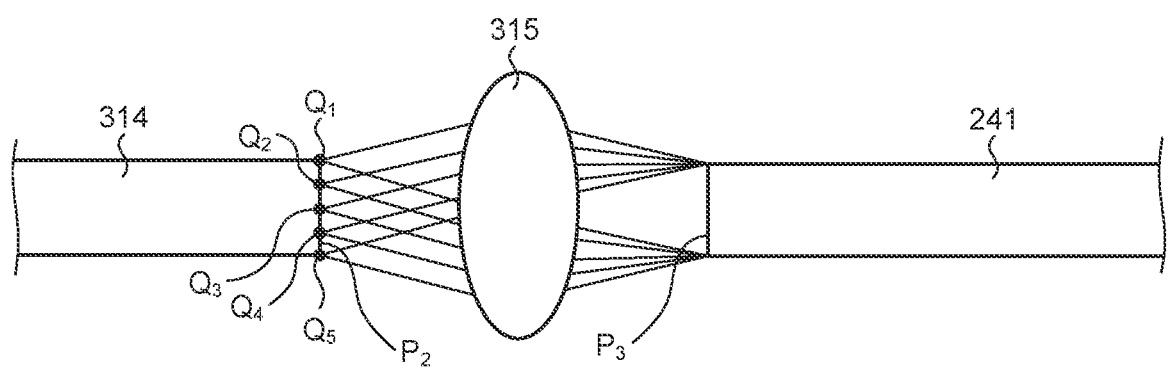
FIG. 12 is a diagram illustrating an example of light guiding in the rod, a pupil generating lens, and a light guide that are included in an illumination optical system.
Figure 13:
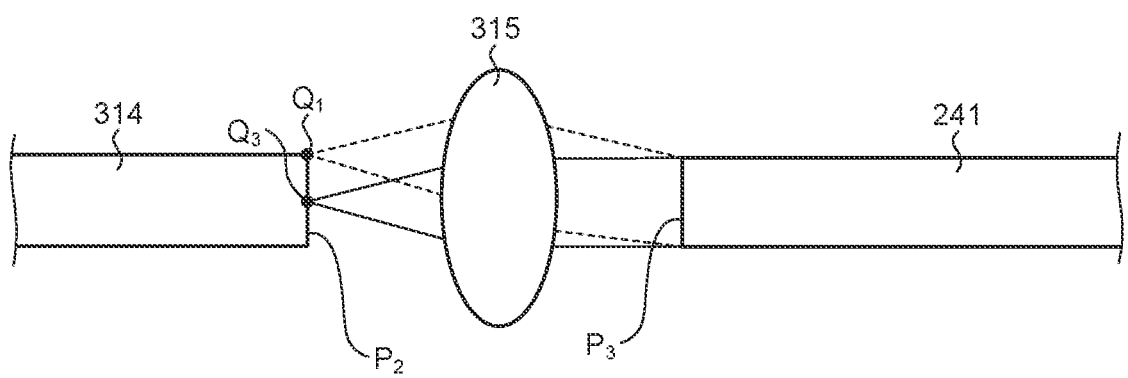
FIG. 13 is a diagram illustrating an example of light guiding in the rod, the pupil generating lens, and the light guide that are included in the illumination optical system.

Functions of the pupil generating lens 315 will be described next by reference to FIG. 12 and FIG. 13. FIG. 12 and FIG. 13 are diagrams illustrating an example of light guiding in the rod, the pupil generating lens, and the light guide that are included in the illumination optical system.

Light beams emitted from the exit end face $P_2$ of the rod 314 and input to the entrance end face $P_3$ of the light guide 241 via the pupil generating lens 315 are equal in intensity regardless of the angles at which the light beams enter the light guide 241. For example, light beams respectively emitted from points $Q_1$ to $Q_5$ (see FIG. 12) at positions different from each other on the exit end face $P_2$ are respectively input to the entrance end face $P_2$ of the light guide 241 via the pupil generating lens 315. These light beams have different incident angles to the light guide 241 depending on their positions on the exit end face $P_2$. For example, the light beam (broken line) emitted from the point $Q_1$ illustrated in FIG. 13 and the light beam (solid line) emitted from the point $Q_3$ are incident on the entrance end face $P_3$ at different angles. If different points (for example, the points $Q_1$ to $Q_5$) are equal in intensity, light beams incident on the entrance end face $P_3$ of the light guide 241 are supposed to be equal in intensity even if they have different incident angles. That is, because the intensity distribution on the exit end face $P_2$ is approximately uniform due to the effect of the rod 314 to uniformize the spatial intensity distribution, the points $Q_1$ to $Q_5$ are approximately equal in intensity, and as a result, light beams having optical intensities low in dependence on the angles and thus do not vary in intensity depending on the incident angles are incident on the entrance end face $P_3$ of the light guide 241. Light beams guided through the light guide 241 supply illumination light having a uniform light distribution from a distal end of the light guide 241. Light beams incident on the optical fibers forming the light guide 241 are approximately equal in intensity.

In the first embodiment described above, light beams respectively emitted from the plural light sources 311 are condensed onto the rod 314 and are reflected inside the rod 314, and light uniform in spatial intensity distribution is thereby generated at the exit end face (the exit end face $P_2$) of the rod 314. This light having a uniform spatial intensity distribution is input to the entrance end face $P_3$ of the light guide 241 arranged at the position of the pupil generated by the pupil generating lens 315, via the pupil generating lens 315. Light beams having the same spatial intensity distribution are input to the entrance end face $P_3$ of the light guide 241 regardless of their positions at the exit end face $P_2$ of the rod 314. Therefore, even if the light sources 311 are selectively turned on or off by adjustment of light quantity, for example, the angular intensity distribution of light incident on the light guide 241 substantially does not change. According to the first embodiment, even if plural light sources are independently controlled, illumination light that does not change in light distribution and uniform in illumination distribution is able to be emitted.

Figure 14:
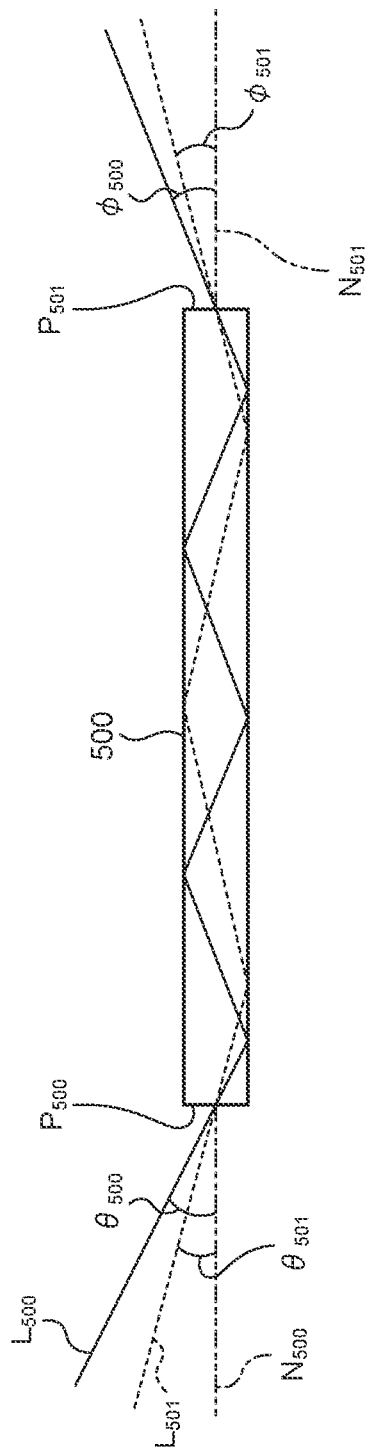
FIG. 14 is a diagram illustrating incident angles and output angles of light beams at a light guide.

In contrast, known illumination devices are sometimes unable to illuminate subjects uniformly when the distribution of light changes and the distribution of light emitted outside becomes uneven. FIG. 14 is a diagram illustrating incident angles and output angles of light beams at a light guide (for example, a single optical fiber). A light beam $L_{500}$ and a light beam $L_{501}$ respectively represent traveling paths of light beams positioned in the centers of light (light fluxes) emitted from light sources different from each other. For example, the light beam $L_{500}$ incident at an incident angle $A_{500}$ with respect to an axis $N_{500}$ orthogonal to an entrance end face $P_{500}$ propagates through the light guide 500 and is output at an output angle $\phi_{500}$ with respect to an axis $N_{501}$ orthogonal to an exit end face $P_{501}$. The light beam $L_{501}$ incident at an incident angle $\theta_{501}$ ($<\theta_{500}$) with respect to the axis $N_{500}$ propagates through the light guide 500 and is output at an output angle $\phi_{501}$ ($<\phi_{500}$) with respect to the axis $N_{501}$. As indicated by FIG. 14, when the incident angles of light beams incident on the light guide 500 are different, the light beams output from the light guide 500 have different light distributions. The incident angles and the output angles may differ due to a bend in the fiber, for example, but light beams are output with their magnitude relations among the incident angles maintained.

Figure 22A:
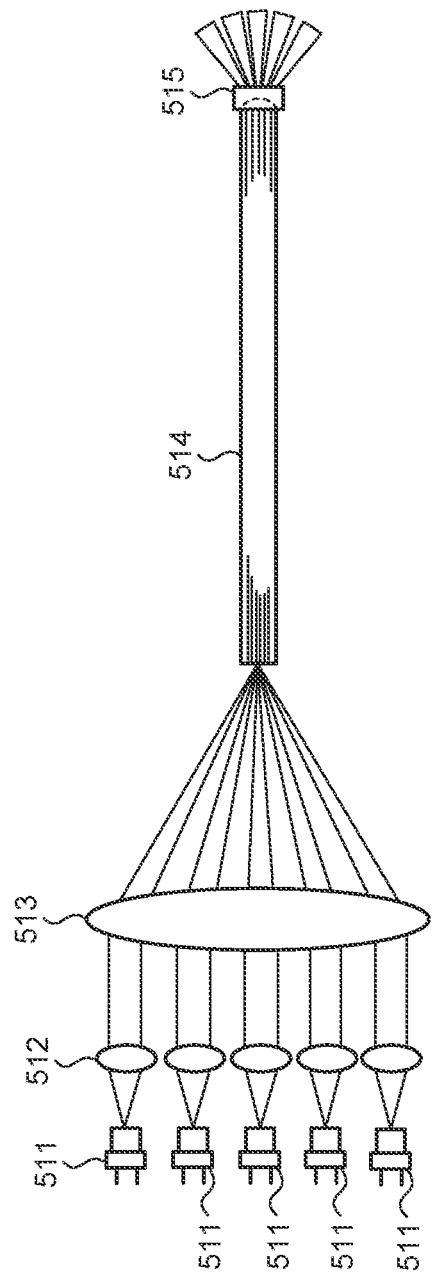
FIG. 22A is a diagram illustrating light sources turned on according to a known illumination technique and a light distribution thereof.
Figure 22C:
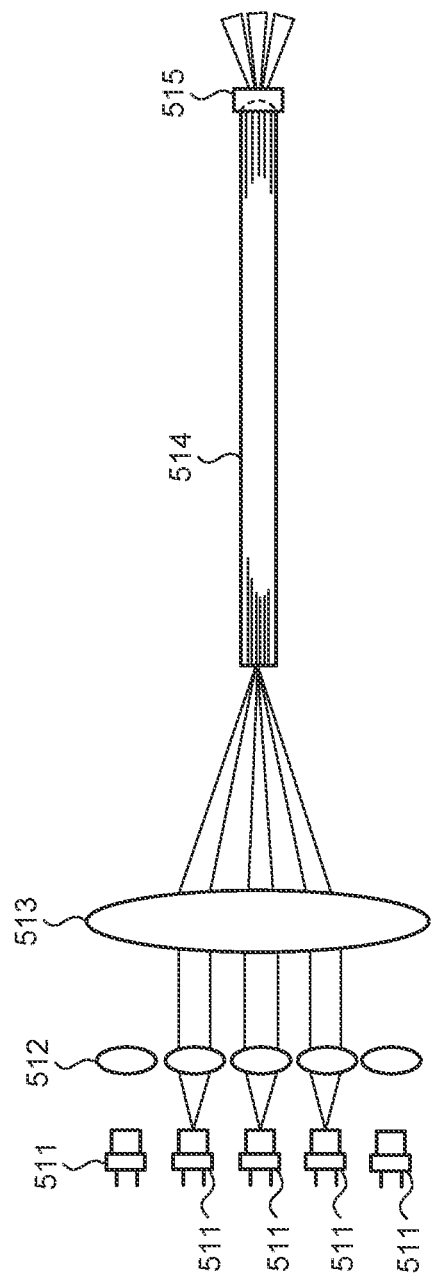
FIG. 22C is a diagram illustrating light sources turned on according to the known illumination technique and a light distribution thereof.

A known illumination device includes, for example, plural light sources 511, plural collimator lenses 512 provided correspondingly to the light sources 511, a condenser lens 513 that condenses approximately collimated light beams that have passed through the collimator lenses 512, a light guide 514 to which the light beams condensed by the condenser lens 513 are input, and an illumination lens 515 that guides the light beams output by the light guide 514. FIG. 22A to FIG. 22C illustrate different lighting patterns for the plural light sources 511. Specifically, FIG. 22A is a diagram illustrating the distribution of light emitted from the illumination lens 515 in a case where all of the light sources 511 are turned on in the above described device. FIG. 22B is a diagram illustrating the distribution of light emitted from the illumination lens 515 in a case where the light sources 511 arranged at positions farthest from the center of the condenser lens 513 are turned on in the figure, in the above described device. FIG. 22C is a diagram illustrating the distribution of light in a case where the lighting pattern illustrated in FIG. 22B is reversed in the above described device. As indicated by FIG. 22A to FIG. 22C, when the plural light sources are independently controlled in the known illumination device, the light emitted from the illumination lens 515 has a different light distribution depending on the positions of the light sources that are turned on. Known illumination devices are sometimes unable to illuminate subjects uniformly when the distribution of light changes and becomes uneven.

In the above described first embodiment, the plural light sources may be configured to include plural types of light sources that emit light beams having different wavelength bands.

First Modified Example of First Embodiment

Figure 15:
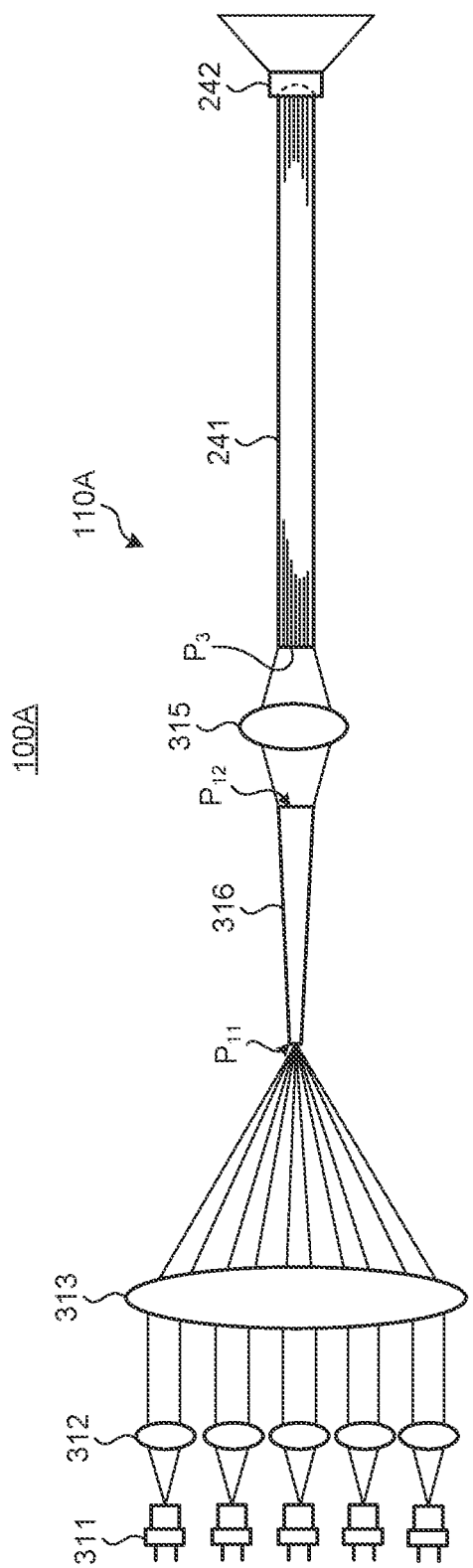
FIG. 15 is a diagram illustrating a configuration of an illumination optical system included in an endoscope system according to a first modified example of the first embodiment.

Next, a first modified example of the first embodiment will be described by reference to FIG. 15 to FIG. 17. FIG. 15 is a diagram illustrating a configuration of an illumination device included in an endoscope system according to the first modified example of the first embodiment. The endoscope system according to the first modified example has a configuration that is the same as that of the endoscope system 1 described above, except for the rod in the light source device 3 of the endoscope system 1. A component (an illumination optical system) different from that of the first embodiment described above will be described below.

An illumination device 100A according to the first modified example includes plural light sources 311, plural collimator lenses 312, a condenser lens 313, a rod 316, a pupil generating lens 315, a light guide 241, and an illumination lens 242. Furthermore, in this first modified example, the collimator lenses 312, the condenser lens 313, the rod 316, the pupil generating lens 315, the light guide 241, and the illumination lens 242 form an illumination optical system 110A. The rod 316 corresponds to a first light guiding member. The rod 316 having a configuration different from that of the first embodiment described above will be described below.

The rod 316 is provided at the condensing position of the condenser lens 313 and light condensed by the condenser lens 313 is input to the rod 316. The rod 316 has an entrance end face $P_{11}$ to which light from the condenser lens 313 is input, and an exit end face $P_{12}$ which is provided opposite to the entrance end face $P_{11}$ and from which the light that has entered the rod 316 is output, and the rod 316 guides the light from the entrance end face $P_{11}$ to the exit end face $P_{12}$ while reflecting the light. The entrance end face $P_{11}$ has an area smaller than that of the exit end face $P_{12}$. That is, the rod 316 has a tapered shape that decreases in sectional area from the entrance end face $P_{11}$ toward the exit end face $P_{12}$. The rod 316 is formed using a rod integrator that uniformizes the spatial intensity distribution of light at the exit end face.

Light beams from the light sources 311 are mixed by entering the rod 316 via the collimator lenses 312 and condenser lens 313 and repeating reflection inside the rod 316, and light uniform in spatial intensity distribution is thereby generated.

Figure 16:
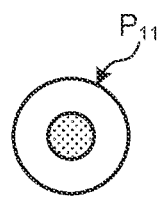
FIG. 16 is a diagram illustrating a distribution of light at an entrance end face $P_{11}$ illustrated in FIG. 15.
Figure 17:
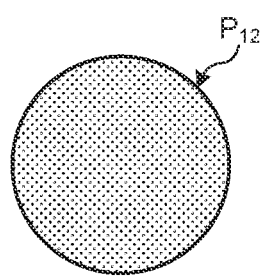
FIG. 17 is a diagram illustrating a distribution of light at an exit end face $P_{12}$ illustrated in FIG. 15.

FIG. 16 is a diagram illustrating the distribution of light at the entrance end face $P_{11}$ illustrated in FIG. 15. FIG. 17 is a diagram illustrating the distribution of light at the exit end face $P_{12}$ illustrated in FIG. 15. Light that is input to the entrance end face $P_1$ has been condensed by the condenser lens 313 and is thus distributed to a part (in a central portion in FIG. 16) of the entrance end face $P_{11}$. In contrast, light that has reached the exit end face $P_{12}$ via the interior of the rod 316 is distributed over the whole exit end face $P_{12}$ (see FIG. 17). By traveling through the rod 316, the light becomes uniform in spatial intensity distribution.

The light that has become uniform in spatial intensity distribution enters the light guide 241 via the pupil generating lens 315.

The first modified example described above is able to achieve the above described effects of the first embodiment, and the uniformizing effect of the light guiding system is able to be increased by: the rod 316 having the tapered shape with the entrance end face having an area smaller than the area of the exit end face; and the number of times of reflection of light in the rod 316 thereby being increased as compared to that in a columnar rod having a uniform cross section. Increasing the uniformizing effect of the light guiding system in the rod 316 enables decrease in the longitudinal length of the rod 316 (corresponding to the length L described above) and, as a result, downsizing of the illumination device 100A.

Second Modified Example of First Embodiment

Figure 18:
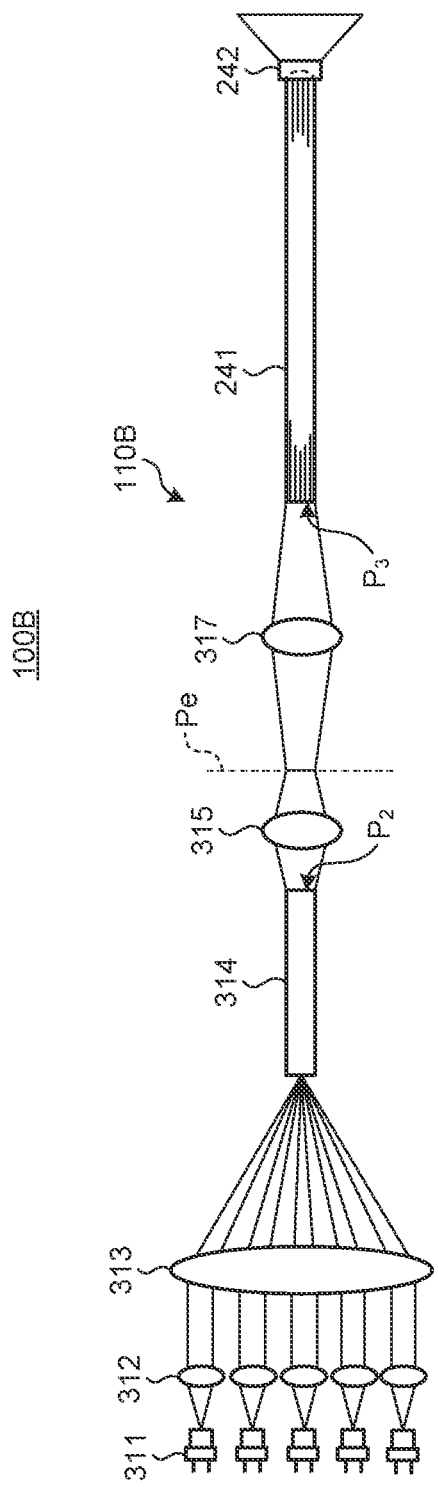
FIG. 18 is a diagram illustrating a configuration of an illumination device included in an endoscope system according to a second modified example of the first embodiment.

Next, a second modified example of the first embodiment will be described by reference to FIG. 18. FIG. 18 is a diagram illustrating a configuration of an illumination optical system included in an endoscope system according to the second modified example of the first embodiment. The endoscope system according to the second modified example has a configuration that is the same as that of the endoscope system 1 described above, except for the configuration of the illumination optical system in the endoscope system 1. A component (an illumination optical system) different from that of the first embodiment described above will be described below.

An illumination device 100B according to the second modified example includes plural light sources 311, plural collimator lenses 312, a condenser lens 313, a rod 314, a pupil generating lens 315, a pupil relay lens 317, a light guide 241, and an illumination lens 242. In this second modified example, the collimator lenses 312, the condenser lens 313, the rod 314, the pupil generating lens 315, the pupil relay lens 317, the light guide 241, and the illumination lens 242 form an illumination optical system 110B. The pupil relay lens 317 may be provided near a light source device or provided near the light guide 241. Furthermore, the rod 314 may be replaced by the rod 316 according to the first modified example. The pupil relay lens 317 having a configuration different from that of the first embodiment described above will be described below.

The pupil relay lens 317 is provided between the pupil generating lens 315 and the light guide 241 and relays the pupil generated by the pupil generating lens 315. In the illumination device 100B, an entrance end face $P_3$ of the light guide 241 is arranged at the position of the pupil relayed and generated by the pupil relay lens 317. That is, the entrance end face $P_3$ of the light guide 241 is arranged at a position (a pupil plane relayed and generated by the pupil relay lens 317) that is conjugate to the pupil (pupil plane Pe) generated by the pupil generating lens 315. In this second modified example, the pupil generating lens 315 and pupil relay lens 317 correspond to a Kohler illumination unit. An example where a single pupil relay lens 317 is provided has been described with respect to this second modified example, but plural pupil relay lenses 317 may be provided instead. The entrance end face $P_3$ of the light guide 241 is arranged in a pupil plane region near and including the pupil plane of the whole optical system from the condenser lens 313 to the Kohler illumination unit.

Light beams from the light sources 311 are mixed by entering the rod 314 via the collimator lenses 312 and condenser lens 313 and repeating reflection inside the rod 314, and light uniform in spatial intensity distribution is thereby generated. The light that has become uniform in spatial intensity distribution enters the light guide 241 via the pupil generating lens 315 and pupil relay lens 317.

In the second modified example described above, light beams respectively emitted from the plural light sources 311 are condensed onto the rod 314 and are reflected inside the rod 314, and light uniform in spatial intensity distribution is thereby generated at the exit end face (exit end face $P_2$) of the rod 314. This light uniform in spatial intensity distribution is input to the entrance end face $P_3$ of the light guide 241 arranged at the position conjugate to the pupil generated by the pupil generating lens 315, via the pupil generating lens 315 and pupil relay lens 317. Light beams having the same intensity are input to the entrance end face $P_3$ of the light guide 241 regardless of their positions at the exit end face $P_2$ of the rod 314, that is, their incident angles on the entrance end face $P_3$. Therefore, even when the light sources are selectively turned on or off by adjustment of light quantity, for example, intensities of light beams incident on the light guide 241 do not change depending on their incident angles and are low in dependence on their angles. According to the second modified example, even when plural light sources are independently controlled, illumination light that does not change in light distribution and is uniform in illumination distribution is able to be emitted.

Second Embodiment

Figure 19:
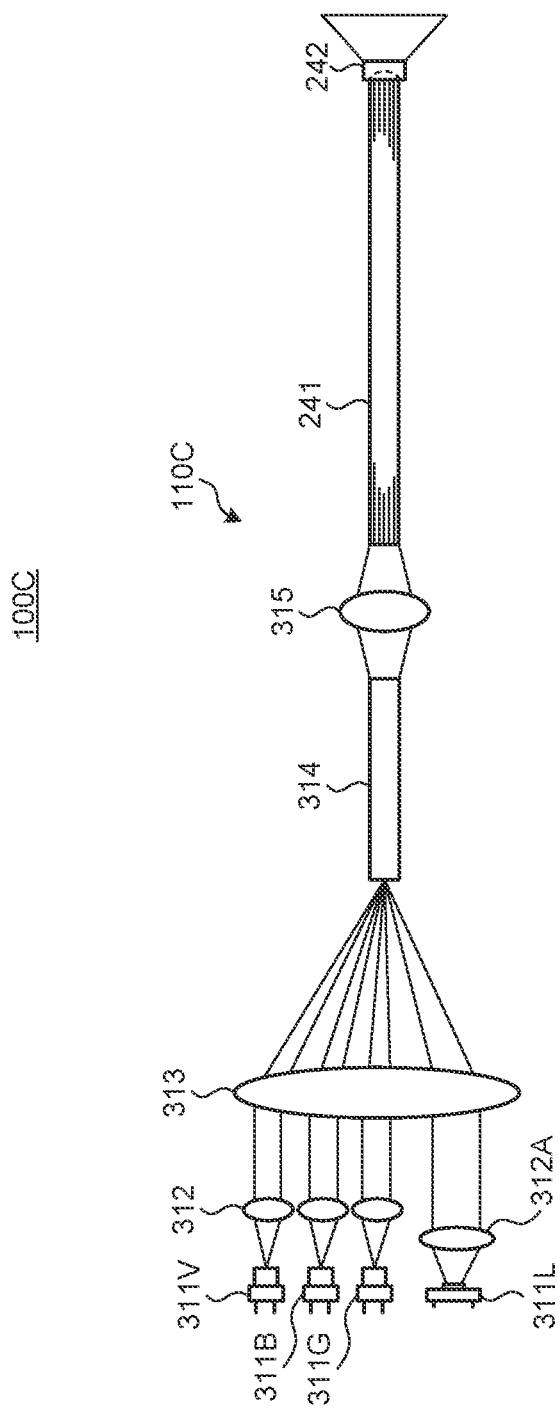
FIG. 19 is a diagram illustrating a configuration of an illumination device included in an endoscope system according to a second embodiment.

Next, a second embodiment will be described by reference to FIG. 19. FIG. 19 is a diagram illustrating a configuration of an illumination optical system included in an endoscope system according to the second embodiment. The endoscope system according to the second embodiment has a configuration that is the same as that of the endoscope system 1 described above, except for the configuration of the illumination optical system in the endoscope system 1. A component (an illumination optical system) different from that of the first embodiment described above will be described below.

An illumination device 100C according to the second embodiment includes plural light sources (a first light source 311V, a second light source 311B, a third light source 311G, and a fourth light source 311L), plural collimator lenses (collimator lenses 312 and 312A), a condenser lens 313, a rod 314, a pupil generating lens 315, a light guide 241, and an illumination lens 242. In this second embodiment, the collimator lenses (collimator lenses 312 and 312A), the condenser lens 313, the rod 314, the pupil generating lens 315, the light guide 241, and the illumination lens 242 form an illumination optical system 110C. The rod 314 may be replaced by the rod 316 according to the first modified example. The pupil relay lens 317 according to the second modified example may also be included. The light sources having a configuration different from that according to the first embodiment described above will be described below.

The first light source 311V emits light (violet illumination light) of a wavelength band of 380 nm to 450 nm.

The second light source 311B emits light (blue illumination light) of a wavelength band of 450 nm to 495 nm.

The third light source 311G emits light (green illumination light) of a wavelength band of 495 nm to 570 nm.

The first light source 311V, the second light source 311B, and the third light source 311G are formed using semiconductor lasers (semiconductor light sources).

The fourth light source 311L emits light (red illumination light) of a wavelength band of 570 nm to 750 nm. The fourth light source 311L is formed using a light source lower in directivity than the first light source 311V, second light source 311B, and third light source 311G, for example, a light emitting diode (LED) light source. The fourth light source 311L has light distribution characteristics different from those of the first light source 311V, the second light source 311B, and the third light source 311G.

The first light source 311V to fourth light source 311L may have the same amount of emission, for example, the same maximum amount of emission, or the amount of emission of at least some of the light sources may be different from the amount of emission of the other light sources.

The collimator lenses 312 are provided correspondingly to the first light source 311V, second light source 311B, and third light source 311G, and form illumination light emitted by these light sources into collimated light.

The collimator lens 312A is provided correspondingly to the fourth light source 311L and forms illumination light emitted by the fourth light source 311L into collimated light.

Light beams emitted by these light sources enter the rod 314 via the collimator lenses and the condenser lens 313, are reflected inside the rod 314, and are thereby mixed, and light uniform in spatial intensity distribution is thereby generated. The light that has become uniform in spatial intensity distribution enters the light guide 241 via the pupil generating lens 315 and pupil relay lens 317.

When the light sources have different beam diameters, light distribution characteristics differ depending on the light sources, and thus in a configuration using a known aspheric lens, light emitted from the illumination lens varies in spatial intensity distribution and distribution of the light becomes uneven. In contrast, uniformizing spatial intensity distributions of light beams from the light sources by using the rod 314 uniformizes the spatial intensity distribution of light emitted from the illumination lens 242 even if each of the light sources is turned on alone or a combination of different types of the light sources is turned on.

In the second embodiment described above, light beams emitted respectively from plural light sources having different emission wavelength bands or different types of solid-state light sources are condensed onto the rod 314 and reflected in the rod 314, and light uniform in spatial intensity distribution is thereby generated at the exit end face of the rod 314. This light having a uniform spatial intensity distribution is input to the entrance end face of the light guide 241 arranged at the position of the pupil generated by the pupil generating lens 315, via the pupil generating lens 315. Light beams having the same spatial intensity distribution are input to the entrance end face of the light guide 241 regardless of their positions at the exit end face of the rod 314. Therefore, even when the light sources are selectively turned on or off by adjustment of light quantity, for example, intensities of light beams incident on the light guide 241 do no change depending on their incident angles and are low in dependence on the angles. According to the second embodiment, even if plural light sources are independently controlled, illumination light that does not change in light distribution and uniform in illumination distribution is able to be emitted.

Modes for implementing the present disclosure have been described thus far, but the present disclosure should not be limited to the embodiments described above only. The present disclosure may include various embodiments not described herein.

Figure 20:
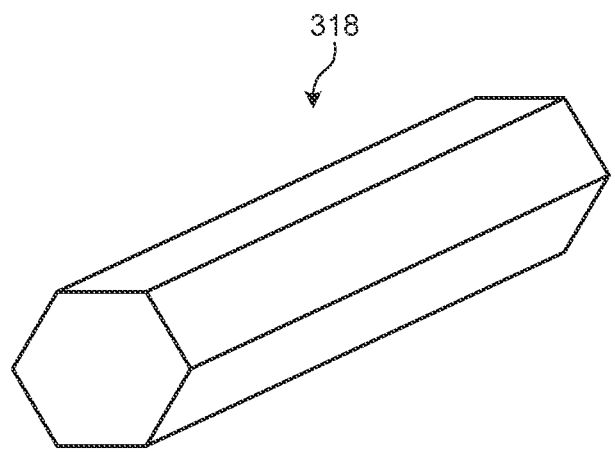
FIG. 20 is a perspective view illustrating another example of the rod according to the embodiments.
Figure 21:
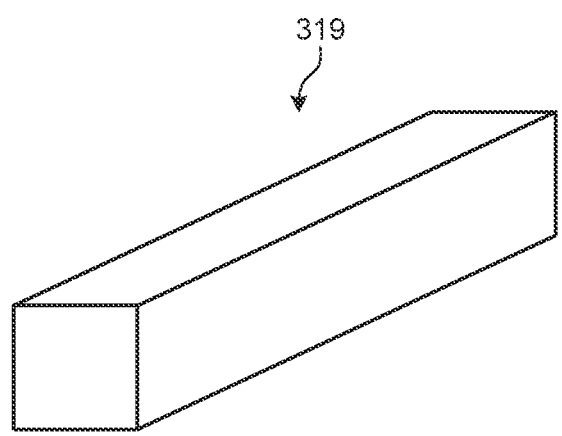
FIG. 21 is a perspective view illustrating another example of the rod according to the embodiments.

With respect to the first and second embodiments, the examples where the rods are cylindrical have been described above, but the end faces and cross sections of the rods are not necessarily circular. For example, the rods may each be a rod 319 having hexagonal end faces and cross section illustrated in FIG. 20 or a rod 318 having rectangular end faces and cross section illustrated in FIG. 21.

Furthermore, with respect to the first and second embodiments, the examples where the light guides 241 are each formed of plural optical fibers have been described above, but the light guide 241 may be formed using a rod instead of optical fibers.

Furthermore, according to the above description of the first and second embodiments, the light source device 3 is configured to be separately bodied from the endoscope 2, but a light source device may be provided in the endoscope 2 by, for example, providing a semiconductor laser at a distal end of the endoscope 2. In addition, functions of the processing device 5 may be provided in the endoscope 2.

Furthermore, according to the above description of the first and second embodiments, the light source device 3 is separately bodied from the processing device 5, but the light source device 3 and the processing device 5 may be integrated with each other, and the light source unit 31, the light source driver 32, and the illumination control unit 33 may be provided inside the processing device 5, for example.

Furthermore, according to the above description of the first and second embodiments, the endoscope system according to the present disclosure is the endoscope system 1 using the flexible endoscope 2 for observation of body tissue inside subjects, but the endoscope system may be an endoscope system using a rigid endoscope, an industrial endoscope for observation of characteristics of materials, a capsule endoscope, a fiberscope, or a camera head connected to an eyepiece unit of an optical endoscope, such as an optical viewing tube.

An illumination optical system and an illumination device according to the present disclosure are useful for illumination with reduced change in light distribution even when plural light sources are independently controlled.

The present disclosure has an effect of enabling illumination with reduced change in light distribution even when plural light sources are independently controlled.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An illumination optical system comprising:
a condenser lens configured to condense plural light fluxes incident on different positions on a surface of the condenser lens;
a first light guide comprising:
a first entrance end face to which light condensed by the condenser lens is input, and
a first exit end face from which the light is output,
the first light guide being configured to
guide the light input to the first entrance end face by reflecting the light inside the condenser lens, and
output the light from the first exit end face;
a pupil generating lens to which the light output from the first exit end face is input, the pupil generating lens being configured to generate a pupil with the first exit end face serving as an object surface; and
a second light guide comprising:
a second entrance end face arranged at a position of the pupil or a position conjugate to the position of the pupil, the light passed through the pupil generating lens being input to the second entrance end face, and
a second exit end face from which the light that input to the second entrance end face is output,
the second light guide being configured to:
guide the light input to the second entrance end face by reflecting the light inside the second light guide, and
output the light from the second exit end face.

2. An illumination optical system comprising:
a condenser lens configured to condense plural light fluxes incident on different positions on a surface of the condenser lens;
a first light guide comprising:
a first entrance end face to which light condensed by the condenser lens is input, and
a first exit end face from which the light is output,
the first light guide being configured to:
guide the light input to the first entrance end face by reflecting the light inside the condenser lens, and
output the light from the first exit end face;
a pupil generating lens to which the light output from the first exit end face is input, the pupil generating lens having a focal position, toward the first light guide, being arranged at the first exit end face; and
a second light guide comprising:
a second entrance end face arranged at a position of a pupil of the pupil generating lens or a position conjugate to the position of the pupil, the light passed through the pupil generating lens being input to the second entrance end face, and
a second exit end face from which the light is output,
the second light guide being configured to
guide the light input to the second entrance end face by reflecting the light inside the second light guide, and
output the light from the second exit end face.

3. An illumination optical system comprising:
a condenser lens configured to condense plural light fluxes incident on different positions on a surface of the condenser lens;
a first light guide comprising:
a first entrance end face to which light condensed by the condenser lens is input, and
a first exit end face from which the light is output,
the first light guide being configured to:
guide the light input to the first entrance end face by reflecting the light inside the condenser lens, and
output the light from the first exit end face;
a second light guide comprising:
a second entrance end face to which the light output from the first exit end face is input, and
a second exit end face from which the light is output,
the second light guide being configured to:
guide the light input to the second entrance end face by reflecting the light inside the second light guide, and
output the light from the second exit end face; and
a Kohler illumination unit comprising at least one lens configured to provide Kohler illumination to the second entrance end face with the light output from the exit end face, wherein a pupil plane of the whole optical system from the condenser lens to the Kohler illumination unit is arranged at the second entrance end face.

4. The illumination optical system according to any one of claims 1 to 3, wherein the first light guide is a rod integrator configured to emit uniform light intensity distribution in a plane of the first exit end face.

5. The illumination optical system according to any one of claims 1 to 3, wherein the first light guide is a tapered rod integrator in which the first entrance end face has an area smaller than an area of the first exit end face.

6. The illumination optical system according to any one of claims 1 to 3, wherein the second light guide is a fiber bundle having an output angle dependent on an incident angle of light incident on the second entrance end face, the output angle being that of light output from the second exit end face.

7. An illumination device comprising:
the illumination optical system according to any one of claims 1 to 3; and
plural light sources each configured to emit light toward the condenser lens.

8. The illumination device according to claim 7, wherein the plural light sources include two or more light sources of same color.

9. The illumination device according to claim 7, wherein the plural light sources include light sources of two or more types having light distribution characteristics different from each other.

10. The illumination device according to claim 7, wherein the plural light sources include light sources of two or more types that output light of wavelength bands different from each other.

11. The illumination device according to claim 7, wherein the plural light sources include light sources of two or more types having amounts of emission different from each other.

* * * * *